United States Patent
Muehlig et al.

(10) Patent No.: US 7,825,387 B2
(45) Date of Patent: Nov. 2, 2010

(54) METHOD FOR QUANTITATIVE DETERMINATION OF THE SUITABILITY OF CRYSTALS FOR OPTICAL COMPONENTS EXPOSED TO HIGH ENERGY DENSITIES, CRYSTALS GRADED IN THIS WAY AND USES THEREOF

(75) Inventors: Christian Muehlig, Jena (DE); Wolfgang Triebel, Jena-Cospeda (DE); Gabriela Toepfer, Jena (DE); Regina Martin, Jena (DE)

(73) Assignee: Hellma Materials GmbH & Co. KG, Jena (DE)

( * ) Notice: Subject to any disclaimer, the term of this patent is extended or adjusted under 35 U.S.C. 154(b) by 899 days.

(21) Appl. No.: 11/558,728

(22) Filed: Nov. 10, 2006

(65) Prior Publication Data
US 2010/0001208 A1    Jan. 7, 2010

Related U.S. Application Data

(62) Division of application No. 10/909,896, filed on Aug. 2, 2004, now Pat. No. 7,170,069.

(30) Foreign Application Priority Data

Aug. 2, 2003    (DE) ............................... 103 35 457

(51) Int. Cl.
*G01N 21/64*    (2006.01)
(52) U.S. Cl. ................. 250/461.1; 250/459.1; 250/372; 356/318; 356/51
(58) Field of Classification Search ............. 250/459.1, 250/461.1, 372; 356/318, 51
See application file for complete search history.

(56) References Cited

U.S. PATENT DOCUMENTS

| | | | |
|---|---|---|---|
| 6,486,949 B2 * | 11/2002 | Hachfeld et al. | 356/318 |
| 2001/0043331 A1 * | 11/2001 | Rebhan | 356/432 |
| 2002/0105643 A1 * | 8/2002 | Moersen et al. | 356/318 |
| 2003/0007536 A1 * | 1/2003 | Pell et al. | 372/57 |

FOREIGN PATENT DOCUMENTS

| | | |
|---|---|---|
| JP | 2000-349366 | 12/2000 |
| JP | 2001-33379 | 2/2001 |

* cited by examiner

*Primary Examiner*—David P Porta
*Assistant Examiner*—Jessica L Eley
(74) *Attorney, Agent, or Firm*—Michael J. Striker

(57) ABSTRACT

A method is described for quantitative determination of suitability of an optical material, especially alkali halide and alkaline earth halide single crystals, for optical components exposed to high energy densities, especially of pulsed laser light at wavelengths under 250 nm. In this procedure radiation-dependent transmission of the optical material is determined at ultraviolet wavelengths by fluorescence measurements for fluorescence induced by ultraviolet radiation at these ultraviolet wavelengths. This is accomplished by a method including determining an induced fluorescence maximum of a non-linear absorption process, measuring a slope ($|dT/dH|$) of a functional relationship representing the dependence of the radiation-dependent transmission on fluence (H) for the induced fluorescence and determining radiation-dependent transmissions from this slope for particular fluence values.

8 Claims, 3 Drawing Sheets

METHOD FOR QUANTITATIVE DETERMINATION OF THE SUITABILITY OF CRYSTALS FOR OPTICAL COMPONENTS EXPOSED TO HIGH ENERGY DENSITIES, CRYSTALS GRADED IN THIS WAY AND USES THEREOF

CROSS-REFERENCE

This is a divisional of U.S. patent application Ser. No. 10/909,896 filed on Aug. 2, 2004 now U.S. Pat. No. 7,170,069. This divisional claims the benefit of the filing date of this prior U.S. Patent Application under 35 U.S.C. 120, which, in turn, claims the benefit of the filing date of German Patent Application DE 103 35 457.3 under 35 U.S.C. 119.

BACKGROUND OF THE INVENTION

1. Field of the Invention

The present invention relates to a method for quantitative determination of the usability of or for grading crystals for optical components exposed to high energy densities, especially in the DUV or VUV, the crystals graded according to this method and their uses.

2. Description of the Related Art

It is known that materials for optical components absorb more or less radiation passing through them, so that the intensities of the radiation is generally less than the incident intensity after passing through these materials. Furthermore additional absorption and scattering effects occur at the surfaces of these materials, which also lead to a reduction of the transmission or permeability of these materials. Also the extent of this absorption not only depends on the wavelengths of the radiation, but also on the energy density and/or the fluence. For optical systems, i.e. for optically transparent systems, however absorption is desirably kept as small as possible, so that systems of this sort and/or their components have a high transmission at least for the respective working wavelength ranges. It is also known that the absorption is the sum of material-specific (intrinsic) components and those components, which are derived from so-called non-intrinsic components, such as inclusions, impurities and/or crystal defects. The intrinsic absorption is represented by a constant of the material, which is independent of the quality of the material and may also not be reduced. However the additional non-intrinsic absorption of the material is dependent on the quality of the material, i.e. the previously named impurities and crystal defects, etc. Thus the non-intrinsic absorption is theoretically avoidable. It leads to a quality loss of the optical material and thus the system.

Energy, which leads to heating, is added to the optical material by both the intrinsic and also the non-intrinsic absorption. This sort of heating of the material has the disadvantage that the optical properties, e.g. the index of refraction, change. This leads e.g. to a change in the imaging behavior in an optical component used for beam formation, since the index of refraction depends on the temperature of the optical material as well as on the wavelength of the light. Furthermore the heating also leads to thermal expansion and thus to a change in the lens geometry. This phenomenon produces a change of the lens focal point and/or a defocusing of images projected with lenses heated in this manner. In photolithography, as it is used for manufacture of computer chips and electronic circuits, this causes an impairment of the quality and/or an increase of waste and thus is undesirable.

In many materials however a part of the absorbed radiation is not only converted into heat, but also into a form of fluorescence. The formation of fluorescence in optical materials, especially in optical crystals, is also known. For example, detection and measurement of laser-induced fluorescence (LIF) in quartz, especially OH-rich quartz and/or in a glass material, has been described. See, for example, in W. Triebel, et al, in "Evaluation of Fused Silica for DUV Laser Applications by Short Time Diagnostics", Proceedings SPIE, Vol. 4103, pp. 1 to 11, (2000). Furthermore formation of optical absorption bands in a calcium fluoride crystal is described by M. Mizuguchi, et al, in J. Vac. Sci. Technol. A, Vol. 16, pp. 2052 to 3057 (1998). Furthermore time-resolved photoluminescence for diagnosis of laser damage in calcium fluoride crystals is described by M. Mizuguchi, et al, in J. Opt. Soc. Am. B, Vol. 16, pp. 1153 to 1159, July 1999. The formation of color centers for producing photoluminescence by excitation with an ArF excimer laser at 193 nm is described. However in order to permit this sort of measurement, crystals with comparatively high impurity content are used, which are not suitable for the stringent requirements of photolithography. Furthermore the fluorescence measurement is first performed after a waiting time of 50 nsec after the laser pulse ends in the sample to be tested. It has been shown that the fluorescence values so obtained could not be used for quality control and/or for determination of the extent of the impurities. Also they could not be used for formation of color centers in crystals of higher quality.

Thus those skilled in the art currently believe that the determination of radiation-induced fluorescence may not be used for quality control of high-quality optical materials, such as highly pure calcium fluoride for photolithography. See also the lecture of Dr. Mann, Laser Work at Göttingen, SPIE Conference in Seattle, U.S.A., July 2002, in SPIE Vol. 4779, pp. 31-40 (2002). According to this reference a correlation between the laser-induced fluorescence and information regarding impurities and/or optical quality of the material is not possible.

The lifetimes and signal strengths of different fluorescence bands of laser-induced fluorescence (LIF) in $CaF_2$ crystals produced by excitation with laser light at 193 nm were described in "Proc. SPIE", 4932, pp. 458-466 (2002) by C. H. Mühlig, W. Triebel, et al. They showed that the induced fluorescence bands at 580 nm and 740 nm have an especially great influence on the non-intrinsic transmission. The greater the proportion of induced fluorescence at these wavelengths, the stronger the non-linear absorption behavior. Moreover they also showed that the induced fluorescence bands with maxima at 313 nm and 333 nm have a radiation induced, i.e. non-linear, absorption.

This reference also describes work that shows that a stationary transmission value is achieved by pre-irradiation of the respective samples with 30,000 laser pulses of high-energy laser radiation of 10 $mJ/cm^2$ at 193 nm.

So-called two-photon absorption processes, which are the origin for so-called "self-trapped-exciton" emissions (STE), are also known, from the work of C. H. Mühlig, W. Triebel, et al, "Proc. SPIE", 4932, pp. 458:466 (2002) as well as M. Mizuguchi, et al, J. Opt. Soc. Am. B, 16, pp. 1153-1159 (1999).

Finally the unpublished WO 2004/027395 of the present inventors describes a method for qualitative evaluation of optical materials. This method comprises determination of the radiation-induced absorption by means of intrinsic fluorescence and non-intrinsic laser-induced fluorescence (LIF) during or immediately after the incident illuminating pulse, i.e. preferably within a time interval of 50 nsec after termination of the irradiating pulse, Characteristic non-intrinsic absorption originating fluorescence events are detected by this procedure, which would not be detected by earlier methods, i.e. by measurements in a later time interval, in which it would not be detected. In this way it would of course be possible to make qualitative determinations regarding the suitability of materials, but not quantitative assessments regarding the suitability of materials for certain applications. Thus for some applications requirements are more stringent than with others, so that quantification of the test properties leads to better more accurate grading and selection of optical materials for later usage at an earlier time.

SUMMARY OF THE INVENTION

It is an object of the present invention to provide a method, which permits a quantitative evaluation of the non-intrinsic absorption, especially the absorption induced by the fluence, and thus the transmission of the raw material, as well as its suitability for certain applications.

It is also an object of the present invention to provide single crystals, especially alkali or alkaline earth halide single crystals, which are quantitatively graded according to their suitability for making optical components exposed to high energy densities.

This object and others, which will be made more apparent hereinafter, is attained in a method for quantitative determination of suitability of optical materials for optical components exposed to high energy densities, which comprises determining radiation-dependent transmission of the optical materials at ultraviolet wavelengths by fluorescence measurements of fluorescence induced at these ultraviolet wavelengths.

According to the invention at least one induced fluorescence maximum of a non-linear absorption process is determined, a slope ($|dT/dH|$) of a curve representing a functional dependence of transmission on fluence (H) for the at least one induced fluorescence maximum is measured and the radiation-dependent transmission is determined from that slope.

According to the invention it was surprisingly found that the radiation-induced absorption, especially the absorption that depends on the fluence, correlates directly with the intensity level in the fluorescence spectra. Thus the absorption or the transmission T for an arbitrary energy density H may be derived with the help of the fluorescence intensity level. Thus the method of invention starts by normalizing the intensities of the fluorescence spectrum, especially of the bands to be observed. This occurs appropriately by means of an intrinsic fluorescence intensity band. A preferred intrinsic fluorescence band has a maximum at 278 nm. A radiation-induced fluorescence band normalized in this manner is a direct measure of the magnitude of $dT/dH$ (the rate of change of the transmission T with respect to the fluence H). According to the invention it was found that the slope of the curve representing the functional relationship between T and H is directly correlated with the intensity of the associated induced fluorescence bands and increases to the same extent as the intensity of the induced fluorescence bands.

According to the invention the slope or the magnitude of the slope is determined from the functional dependence of the transmission (usually in %) on the incident fluence H. Then it is plotted for different samples of different quality by means of the normalized intensities, as shown in FIG. 2. A smooth curve that best fits this data, which serves as a measure of or calibration curve for validation of the arbitrarily changed samples of the same material, may be obtained preferably by curve fitting from the values so obtained, as is shown, for example, in FIG. 4.

In an appropriate embodiment according to the invention a sample of the material to be tested is pre-treated with a high-energy beam. The pre-treatment is performed in a suitable embodiment until an at least approximate saturation of the so-called damage process, especially the rapid damage or also rapid annealing, is reached. These so-called damage-forming color centers arise by absorption at crystal defects and by absorption at foreign atoms embedded in the crystal. The number of color centers increase with the amount of input light or electromagnetic radiation until all possible color centers are formed. These type of color centers are comparatively stable and are maintained usually over a time interval of a half hour to several days and if necessary months. Heating can accelerate the relaxation of such centers.

It has been shown that the absorption at the beginning of irradiation can change surface processes, especially impurities or deposits, which are removed by energy-rich radiation, which are responsible for the extrapolated transmission value $T_0$. They are responsible for a change of the extrapolated transmission value $T_0$ (the transmission as fluence approaches 0). Otherwise the impurities and deposits produce the $T_0$ value.

Preferred radiation wavelengths are those, which should be used in the later used optics. Especially UV and deep UV radiation is used, in which the wavelengths are under 250 nm and especially under 200 nm. Especially laser light with wavelengths of 193 nm and 157 nm are particularly preferred.

The sample should be pre-radiated with at least 20,000, preferably at least 40,000 and especially preferably at least 60,000 laser pulses at 157 nm prior to the start of the determination. Usually the sample is pre-radiated with a beam of at least 70,000, especially at least 100,000 to 150,000 laser pulses. Two hundred thousand laser pulses are totally preferred. The irradiation to saturation of laser damage preferably occurs with a laser producing laser pulses at a wavelength 193 nm with at least 3,000, and especially 4,000, laser pulses. However 5,000 laser pulses have proven to be suitable. In most cases irradiation with 6,000 laser pulses has been an aid to reliability. The laser pulses preferably have a fluence of at least 5 $mJ/cm^2$, especially at least 10 $mJ/cm^2$. Maximum values can preferably amount to 50 $mJ/cm^2$, however preferably amount to 40 $mJ/cm^2$ on the other hand, maximum values of 30, and especially of 20 $mJ/cm^2$, are especially preferred. A fluence of 10 $mJ/cm^2$ has proven to be especially suitable. Preferably, however not necessarily, the same pulse duration and pulse frequency, etc. are used, as are used during the later passage of radiation through the optical material.

It has proven suitable when the measurement with respect to the start of the pulse already starts during the pulse and at the latest after a decay time of 90% of the fluorescence lifetime, especially at most 70% or half of the fluorescence lifetime. This amounts to at maximum 60 nanoseconds after the end of the laser pulse, preferably at maximum 40 and especially 30 nanoseconds, for the relevant fluorescent bands preferred in the procedure according to the invention. A value of 20 seconds is totally preferred for the time interval between the end of the laser pulse and the start of measurement. The induced fluorescence band is already determined during the duration of the pulse in a totally preferred embodiment of the method according to the invention, i.e. simultaneous excited and synchronously measured. In this way a so-called steady state mechanism is attained.

According to the invention it was surprisingly found that the slope of the dT/dH curve or the rate of change of transmission with respect to fluence is comparable for laser radiation at 157 nm and 193 nm. This means that it is possible to establish the general usability, also at other wavelengths, by means of a single determination of the fluorescence by using radiation at one of these two wavelengths. This is indeed surprising from the prior art since no correlation was to found between absorption behaviors with 193 nm and 157 nm radiation according to Mann, et al, in SPIE Vol 4779 (2002).

According to the invention it has been shown that suitable fluorescence bands occur at 740 nm, 580 nm, 420 nm and at 225 nm and at 365 nm. Preferably the stated values of band maximums have an uncertainty of ±10 nm, preferably ±5 nm.

The method according to the invention is preferably performed as it is described in the unpublished DE-A 102 42 934. The non-intrinsic fluorescence is measured, preferably by means of a grating spectrograph and an I-CCD camera with adjustable exposure interval (intensified charged coupled device). The obtained spectrum is preferably processed under computer control. This sort of measurement and apparatus are known to those skilled in the spectroscopy arts. They are described, for example, by W. Triebel, et al, in Proceedings SPIE Vol. 4103, pp. 1 to 11 (2000), "Evaluation of Fused Silica for DUV Laser Applications by Short Time Diagnostics" or also by Mizuguchi, et al, in J. Opt. Soc. Am. B, Vol. 16, 1153 ff. (July 1999).

According to the invention a masking device is especially preferably arranged between the fluorescing sample to be tested and the fluorescence measurement device, which prevents the throughput of energetic exciting radiation. Various types of such blocking or masking devices, which block the arbitrary excitation wavelength, are known to those skilled in the art. The masking or blocking can occur in many different ways. For example, one possibility is the blocking of this wavelength by means of a grating spectrograph arranged in front of the CCD camera, which divides the incident light into its different wavelengths. It is possible to block or deflect the exciting radiation produced by an energetic radiation source by suitable arrangement and rotation of the spectrograph. However it is also possible to rotate the CCD camera itself relative to the grating spectrograph.

A further possibility is to use a wavelength-specific filter, such as a dielectric thin layer filter, which currently may be selective for arbitrary wavelengths. These types of filters are usually manufactured so that a suitable multilayer reflective coating is applied to a supporting material, which changes the throughput at the desired wavelength.

Such layer filters are preferred for use in the method of the invention. It is necessary that the filters exhibit no self-fluorescence excitation due to the incident light, so that the measurement results are not incorrect.

It has been shown that transmission values, especially internal transmission values, measured by means of the method according to the invention may be added with those obtained by other processes, such as fluorescence at 225 nm, whereby a comparatively accurate predication may be made regarding the later radiation permeability of the materials built into an optical component.

The method according to the invention is suitable for an arbitrary optical material, which produces fluorescence under irradiation. However crystalline optical materials, especially halide or fluoride single crystals are preferred. Alkali and/or alkaline earth fluorides, such as calcium fluoride, barium fluoride, strontium fluoride, lithium fluoride, potassium fluoride and/or sodium fluoride or their mixtures, e.g. $KMgF_3$, are especially preferred.

With the method according to the invention it is thus possible to not only exclude those optical materials from further processing, which have a high non-intrinsic fluorescence, but also to select and classify those materials according to their later use, which are suitable for making optical devices.

The optical materials selected by the method according to the invention are especially suitable for making optical components for DUV lithography, and for making wafers coated with photo lacquer. Thus the optical materials according to the invention are suitable for making electronic equipment. The optical materials found by the selection process according to the invention are useful for making lenses, prisms, light conducting rods, optical windows and optical equipment for DUV lithography, especially for making steppers and excimer lasers. Thus they are useful for making integrated circuits, computer chips, and electronic equipment, as well as computers and other units, which contain such chips and integrated circuits.

BRIEF DESCRIPTION OF THE SEVERAL VIEWS OF THE DRAWING

The objects, features and advantages of the invention will now be illustrated in more detail with the aid of the following description of the preferred embodiments, with reference to the accompanying figures in which.

DETAILED DESCRIPTION OF THE INVENTION

Figure 1:
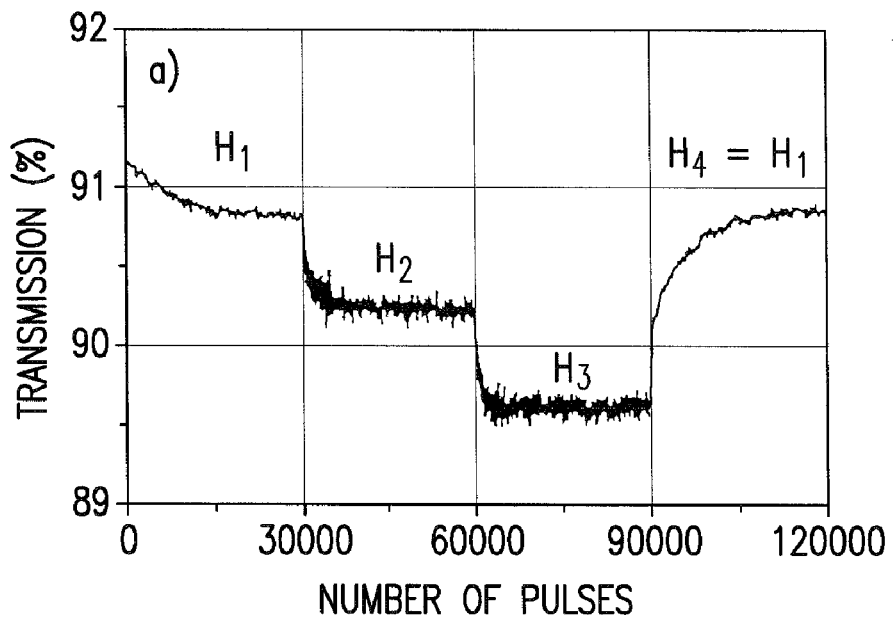
FIG. 1 is a graphical illustration of the behavior of the transmission of a $CaF_2$ single crystal that is irradiated with an ArF laser at 193 nm with respectively increasing fluence.
Figure 2:
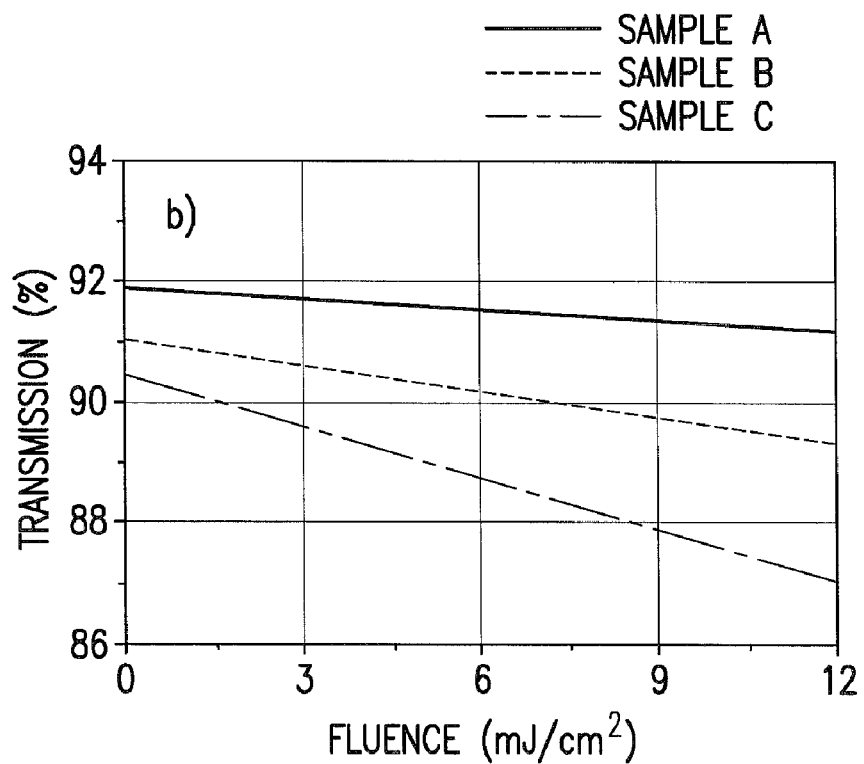
FIG. 2 is a graphical illustration of the dependence of the transmission on the fluence, as determined by the procedure according to FIG. 1.
Figure 3:
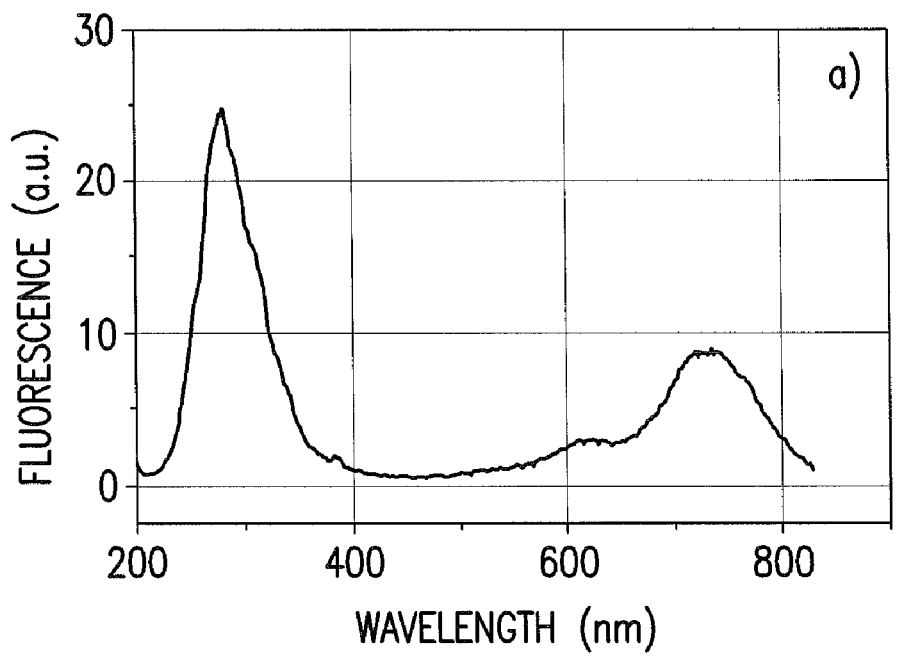
FIG. 3 is a normalized absorption spectrum for the fluorescence of a $CaF_2$ single crystal sample with an intrinsic peak maximum at 278 nm and an intense band at 740 nm.
Figure 4:
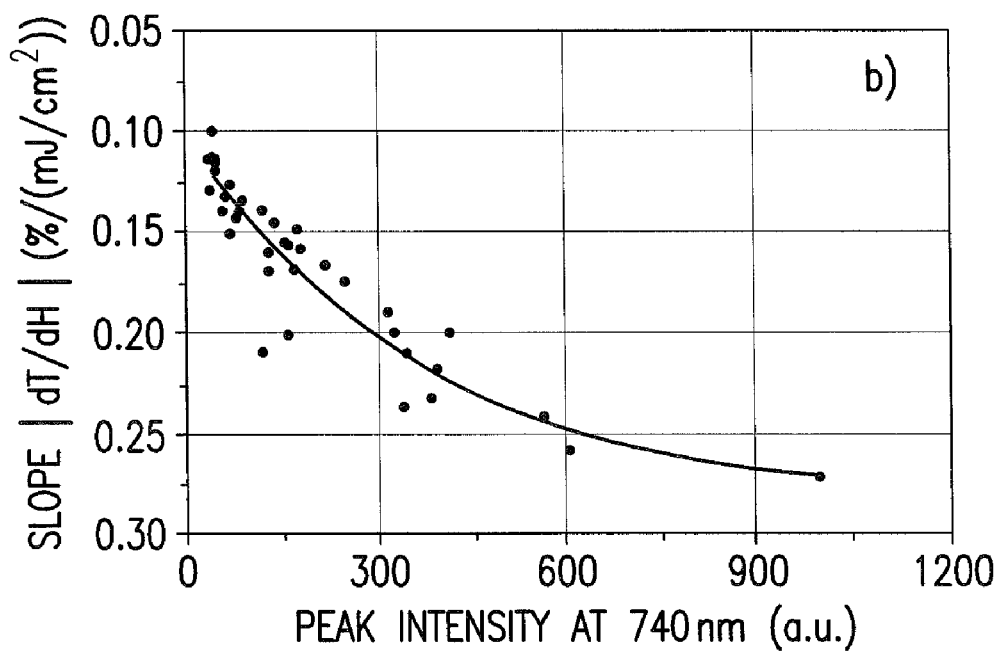
FIG. 4 is a graphical illustration showing dT/dH values as a function of the intensities of the fluorescence peaks of FIG. 3 determined for different samples and a smooth curve fitting this data as determined by a best-fit program.

As shown in FIG. 1, the so-called rapid damage process exhibits saturation after a short increasing stage, going over into saturation with a few thousand laser pulses according to the fluence. The radiation damage remains stable for a relatively long time and relaxes after a half to one hour or up to several days or even months according to the material. Heating accelerates this relaxation process. An additional relaxation process possibility is shown in FIG. 1. Because of the irradiation the rapid damage process due to the increased fluence $H_3$ by means of several thousand laser pulses the transmission may be returned to its original value for the initial fluence $H_1$ (10 $mJ/cm^2$). Different samples A, B and C, which were of the same material, which in the present case is $CaF_2$, were tested by means of the procedure shown in FIG. 1. The different samples have different slopes (rates of change of transmission with respect to fluence) and thus different measures of their usefulness. The slope values dT/dH (where T=transmission and H=fluence) can be determined by means of this sort of curve (FIG. 2). Calibration curves, as shown in FIG. 4, were obtained in this way, as in the example of the LIF (laser-induced fluorescence) for the band at 740 nm. The induced fluorescence was normalized with respect to the intrinsic fluorescence at 278 nm.

With the aid of the curve shown in FIG. 4 it is now possible to determine the fluorescence-dependent transmission of the material by means of a single fluorescence peak intensity measurement in the sample. It is thus possible to give a justification value or grade for the sample according to a particular application. For example if the intensity of the induced fluorescence at 740 nm has a value of about 300, a slope of dT/dH equal to 0.2 results. This value is then used directly as a measure of the usability and as justification criterion. Thus it is arbitrarily possible to set a value of 0.15 or 0.75 as the required justification criterion or grade for a particular application, so that a normalized fluorescence peak intensity of about 200 or about 110 result.

Figure 5:
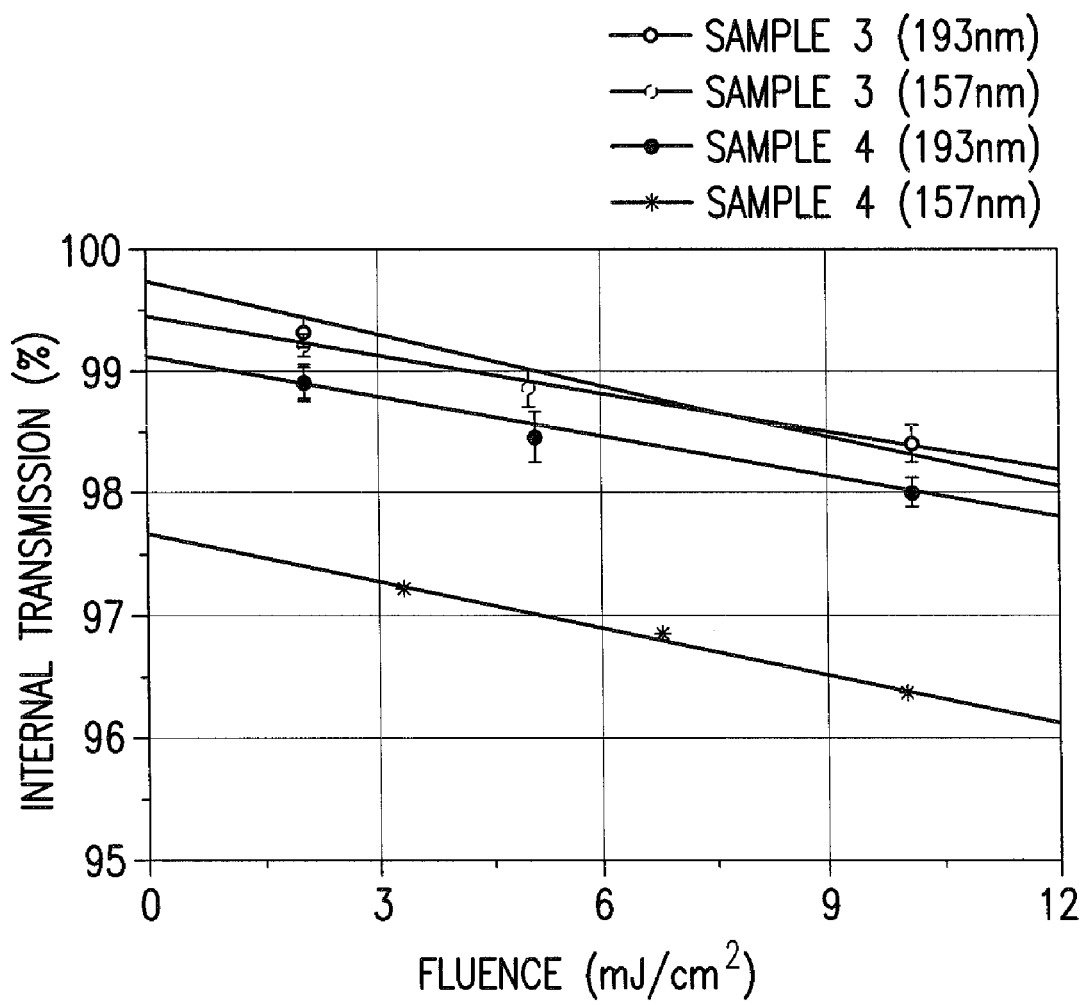
FIG. 5 is a graphical illustration showing dT/dH values for different samples as a function of fluence with an exciting wavelength of 157 nm and 153 nm and a fluence of 10 $mJ/cm^2$.

FIG. 5 shows that the dT/dH values obtained with a wavelength of 193 nm can be translated into the absorption obtained with an excitation wavelength of 153 nm, or vice versa. From this it is also seen that the additional fluorescence band at 225 nm due to irradiation at 157 nm has no influence on the slope of the curves, but does indeed influence the value $T_0$. These bands occur only as impurities in sample 4.

The disclosure in German Patent Application DE 103 35 457.3 of Aug. 2, 2003 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method for quantitative determination of the suitability of crystals for optical components exposed to high energy densities, crystals graded in this way and uses of these crystals, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications Without omitting features that, from the standpoint of prior art, fairly constitute essential characteristics of the generic or specific aspects of this invention.

What is claimed is new and is set forth in the following appended claims.

We claim:

1. A method for quantitative determination of suitability of an optical material for optical components exposed to high energy densities, said method comprising determining radiation-dependent transmission of the optical material at ultraviolet wavelengths by means of fluorescence measurements for fluorescence induced by ultraviolet radiation at said ultraviolet wavelengths;
   wherein at least one induced fluorescence maximum of a non-linear absorption process is determined, a slope ($|dT/dH|$) of a functional relationship representing the dependence of said radiation-dependent transmission on fluence (H) for said at least one induced fluorescence maximum is measured and said radiation-dependent transmission is determined from said slope.

2. The method as defined in claim 1, wherein said radiation-dependent transmission is determined from said slope ($|dT/dH|$) for a predetermined radiation intensity.

3. The method as defined in claim 1, wherein said optical material is irradiated with an energy-rich beam prior to the determining of the radiation-dependent transmission.

4. The method as defined in claim 1, wherein said optical material is irradiated with pulsed laser light and the pulsed laser light comprises at least 5,000 laser pulses.

5. The method as defined in claim 1 or 4, wherein said optical material is pre-radiated with pulsed laser light at a wavelength of 157 nm prior to the determining of the radiation-dependent transmission and the pulsed laser light comprises at least 20,000 laser pulses.

6. The method as defined in claim 4, wherein said slope ($|dT/dH|$) is measured during a laser pulse of said pulsed laser light or at any time until 20 nanoseconds after said laser pulse.

7. The method as defined in claim 1, wherein said at least one fluorescence maximum corresponds to a single fluorescence maximum at a wavelength of 740 nm, 580 nm, 450 nm, 365 nm or 225 nm.

8. The method as defined in claim 1, wherein said slope is measured for a plurality of different samples of said optical material to obtain a number of different slope values, induced fluorescence intensities are measured at said at least one induced fluorescence maximum for said different samples and a calibration curve describing a relationship between said slope values and said induced fluorescence intensities for said different samples is prepared, so that other samples of said optical material can be graded for a particular application by measuring said induced fluorescence intensities for said other samples.

* * * * *